(12) United States Patent
Amorelli et al.

(10) Patent No.: US 8,415,391 B2
(45) Date of Patent: *Apr. 9, 2013

(54) 3.2.1-BICYCLO-OCTENE AND -OCTANE COMPOUNDS

(75) Inventors: Benjamin Amorelli, Farmingdale, NJ (US); Johan Gerwin Lodewijk Pluyter, Middletown, NJ (US); Adam P. Closson, Red Bank, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 274 days.

This patent is subject to a terminal disclaimer.

(21) Appl. No.: 12/901,164

(22) Filed: Oct. 8, 2010

(65) Prior Publication Data

US 2012/0087886 A1  Apr. 12, 2012

(51) Int. Cl.
*A61K 31/22* (2006.01)
*A01N 37/02* (2006.01)
*A01N 37/06* (2006.01)
*A61L 9/01* (2006.01)
*A61L 11/00* (2006.01)

(52) U.S. Cl. ............... 514/546; 510/105; 512/4; 512/8; 560/256

(58) Field of Classification Search .................. 514/546; 510/105; 512/4, 8; 560/256
See application file for complete search history.

(56) References Cited

U.S. PATENT DOCUMENTS 5,958,975 A * 9/1999 Yu et al. .......................... 514/553
7,700,529 B1 * 4/2010 Closson et al. ............... 510/105

* cited by examiner

*Primary Examiner* — Daniel Sullivan
*Assistant Examiner* — Barabara Frazier
(74) *Attorney, Agent, or Firm* — Elizabeth M. Quirk; XuFan Tseng; Joseph F. Leightner

(57) ABSTRACT

The present invention pertains to a method of counteracting a malodor by introducing a malodor counteracting effective amount of a novel 3.2.1-bicyclo-octene or -octane compound represented by formula:

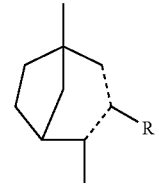

wherein R is selected from the group consisting of hydrogen, acetate, carbonate monomethyl ester, and allyloxy; and wherein the broken line represents a single or double bond.

7 Claims, No Drawings

3.2.1-BICYCLO-OCTENE AND -OCTANE COMPOUNDS

FIELD OF THE INVENTION

The present invention relates to novel chemical entities, a method of using the same as fragrance materials, and a method of using the same as malodor counteracting materials.

BACKGROUND OF THE INVENTION

There is an ongoing need in the fragrance industry to provide new chemicals to give perfumers and other persons the ability to create new fragrances for perfumes, colognes and personal care products.

A particular effort in the fragrance industry has also been made to provide new chemicals to treat and control malodors. "Malodor" is a term used to describe undesirable or unpleasant odor. Common sources of malodors include body perspiration, smoke, environmental odor such as mold and mildew, bathroom, and etc. Conventional perfumes including a variety of fragrance materials are developed to mask malodors, which generally function via two mechanisms: first, the fragrance materials blend with the malodor compound to provide a different and more desirable aroma; and second, the fragrance materials are employed to overwhelm the malodor compound. However, a large quantity of fragrance materials is required for both mechanisms, which in itself is often undesirable. Thus, there remains a need for new chemicals that are effective in counteracting malodors.

SUMMARY OF THE INVENTION

The present invention provides novel 3.2.1-bicyclo-octene and -octane compounds, the unexpected advantageous use thereof in enhancing, improving or modifying the fragrance of perfumes, colognes, toilet waters, fabric care products, personal products, and the like, and the unexpected advantageous use thereof in counteracting malodors.

One embodiment of the invention relates to novel 3.2.1-bicyclo-octene and -octane compounds represented by Formula Ia set forth below:

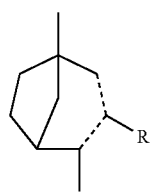

Formula Ia wherein R is selected from the group consisting of hydrogen, acetate, carbonate monomethyl ester, and allyloxy;
and wherein the broken line represents a single or double bond.

Another embodiment of the invention relates to novel 3.2.1-bicyclo-octene and -octane compounds represented by Formula Ib set forth below:

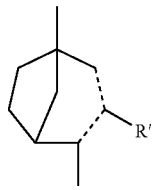

Formula Ib wherein R' is selected from the group consisting of acetate, carbonate monomethyl ester, and allyloxy;
and wherein the broken line represents a single or double bond.

Another embodiment of the invention relates to a method of counteracting a malodor in air space or a substrate comprising the step of introducing a malodor counteracting effective amount of the novel compounds represented by Formula Ia and Formula Ib provided above.

Another embodiment of the invention relates to a malodor counteracting composition comprising the novel compounds represented by Formula Ia and Formula Ib provided above.

These and other embodiments of the present invention will be apparent by reading the following specification.

DETAILED DESCRIPTION OF THE INVENTION

In Formulae Ia above, R is hydrogen, acetate, carbonate monomethyl ester, or allyloxy, and the broken line represents a single or double bond. In Formulae Ib above, R' is acetate, carbonate monomethyl ester, or allyloxy, and the broken line represents a single or double bond.

In one embodiment of the invention, the novel compounds of the present invention are represented by the following structures:

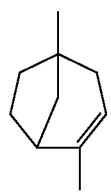

Structure I

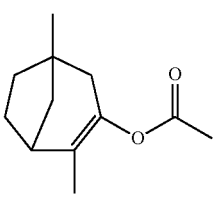

Structure II

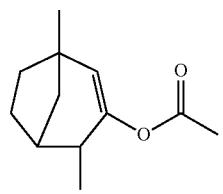

Structure III

3
-continued

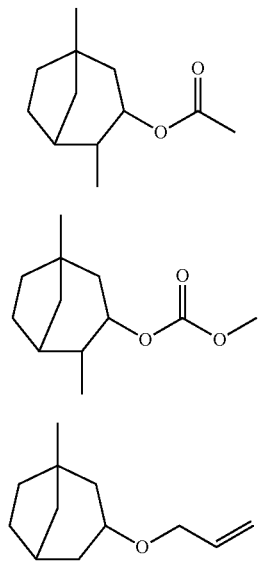

Structure IV

Structure V

Structure VI

4

Those with the skill in the art will appreciate that

Structure I is 2,5-dimethyl-bicyclo[3.2.1]oct-2-ene;

Structure II is acetic acid 2,5-dimethyl-bicyclo[3.2.1]oct-2-en-3-yl ester;

Structure III is acetic acid 1,4-dimethyl-bicyclo[3.2.1]oct-2-en-3-yl ester;

Structure IV is acetic acid 1,4-dimethyl-bicyclo[3.2.1]oct-3-yl ester;

Structure V is carbonic acid 1,4-dimethyl-bicyclo[3.2.1]oct-3-yl ester methyl ester; and Structure VI is 3-allyloxy-1,4-dimethyl-bicyclo[3.2.1]octane.

Novel 3.2.1-bicyclo-octene and -octane compounds of the present invention can be prepared with 1,4-dimethyl-4-vinyl-cyclohexene (commercially available from Evonik Industries) according to a reaction scheme shown as follows:

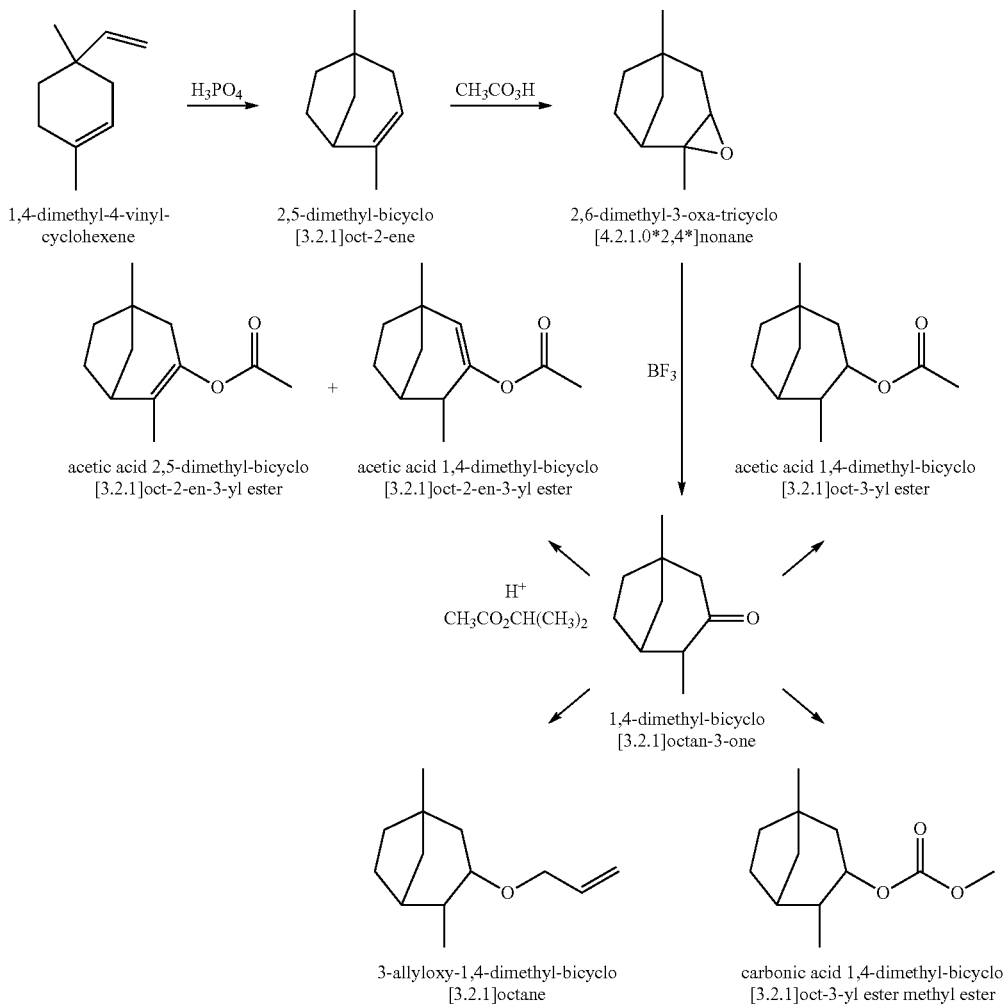

Those with skill in the art will recognize that the compounds of the present invention may have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly silica gel chromatography and solid phase microextraction, referred to as SPME.

The compounds of the present invention are surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. All reagents were purchased from Sigma-Aldrich, Inc. unless otherwise noted. Further, as used herein all percentages are weight percent unless otherwise noted, mol is understood to be mole, μL is understood to be microliter, mL is understood to be milliliter, L is understood to be liter, g is understood to be gram, Kg is understood to be kilogram, oz is understood to be ounce, and mmHg be millimeters (mm) of mercury (Hg). IFF as used in the examples is understood to mean International Flavors & Fragrances Inc., New York, N.Y., USA.

Example I

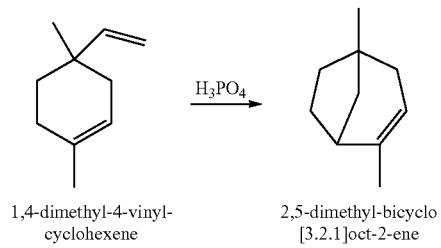

1,4-dimethyl-4-vinyl-cyclohexene      2,5-dimethyl-bicyclo[3.2.1]oct-2-ene

Preparation of 2,5-Dimethyl-bicyclo[3.2.1]oct-2-ene
(Structure I)

Phosphoric acid (145 g, 1.48 mol) was added to a solution of 1,4-dimethyl-4-vinyl-cyclohexene (403 g, 2.96 mol, commercially available from Evonik Industries) in toluene (500 mL) and refluxed for 6 hours. The reaction mixture was subsequently quenched with a solution of sodium hydroxide (NaOH). The organic layer was separated, dried over sodium sulfate (Na$_2$SO4), and fractionated to provide 2,5-dimethyl-bicyclo[3.2.1]oct-2-ene (280 g) having a boiling point of 87° C. at a pressure of 27 mmHg $^1$H NMR: 1.09 ppm (s, 3H), 1.33-1.58 ppm (m, 4H), 1.65 ppm (s, 3H), 1.68-1.82 ppm (m, 3H), 2.08 ppm (d, 1H, J=17 Hz), 2.17 ppm (t, 1H, J=4 Hz), 5.07 ppm (m, 1H)

2,5-Dimethyl-bicyclo[3.2.1]oct-2-ene was described as having green, terpineol, woody, and black pepper notes.

Example II

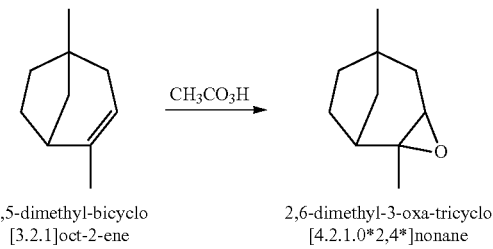

2,5-dimethyl-bicyclo [3.2.1]oct-2-ene     2,6-dimethyl-3-oxa-tricyclo [4.2.1.0*2,4*]nonane Preparation of 2,6-Dimethyl-3-oxa-tricyclo[4.2.1.0*2,4*]nonane 2,5-Dimethyl-bicyclo[3.2.1]oct-2-ene (800 g, 5.88 mol, obtained as above in EXAMPLE I) was fed into a solution of peracetic acid (CH$_3$CO$_3$H, 32%, 1.466 Kg, 6.18 mol) and sodium acetate (CH$_3$CO$_2$Na, 72 g, 0.882 mol), and cooled to 0° C. The reaction mixture was aged for 6 hours, and subsequently quenched with water and toluene. The reaction mixture was shaken and split. The organic layer was first washed with a solution of sodium carbonate (Na$_2$CO$_3$), and then with a solution of sodium sulfite (Na$_2$SO$_3$). Fractional distillation of the organic layer provided 2,6-dimethyl-3-oxa-tricyclo[4.2.1.0*2,4*]nonane (734 g) having a boiling point of 31° C. at a pressure of 18 mmHg $^1$H NMR: 0.92-1.34 ppm (m, 1H), 0.97 ppm (s, 3H), 1.31 ppm (s, 3H), 1.46 ppm (t, 2H, J=7.7 Hz), 1.61 ppm (d, 1H, J=15.0 Hz), 1.68-1.83 ppm (m, 4H), 2.21 ppm (t, 1H, J=5.0 Hz), 2.79 ppm (d, 1H, J=4.6 Hz)

2,6-Dimethyl-3-oxa-tricyclo[4.2.1.0*2,4*]nonane was described as having camphor, woody, fresh, sweet, minty, and thujone-like notes.

Example III

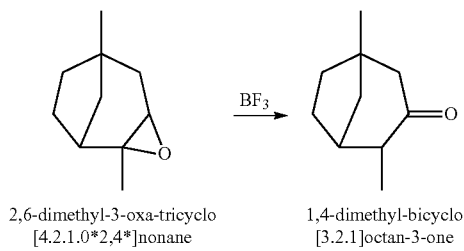

2,6-dimethyl-3-oxa-tricyclo [4.2.1.0*2,4*]nonane     1,4-dimethyl-bicyclo [3.2.1]octan-3-one Preparation of 1,4-Dimethyl-bicyclo[3.2.1]octan-3-one 2,6-Dimethyl-3-oxa-tricyclo[4.2.1.0*2,4*]nonane (381 g, 2.51 mol, obtained as above in EXAMPLE II) was fed into a solution of boron trifluoride diethyletherate (BF$_3$.O(C$_2$H$_5$)$_2$, BF$_3$, 35 g, 0.251 mol) in toluene (500 mL) while the pot temperature was maintained at about 30° C. and the aging process continued for 6 hours. The reaction mixture was subsequently quenched with water and washed with a Na$_2$CO$_3$ solution. Fractional distillation of the organic layer provided 1,4-dimethyl-bicyclo[3.2.1]octan-3-one (337 g) having a boiling point of 43° C. at a pressure of 1 mmHg $^1$H NMR: 0.99 ppm (d, ~34% of 3H, J=6.5 Hz), 1.12 ppm (d, ~66% of 3H, J=6.5 Hz), 1.13 ppm (s, 3H), 1.23-1.54 ppm (m, 4H), 1.62-2.44 ppm (m, 4H), 1.82 ppm (d, ~34% of 1H, J=11.6 Hz), 1.88 ppm (d, ~66% of 1H, J=12.2 Hz), 2.14 ppm (d, ~34% of 1H, J=15.8 Hz)

1,4-Dimethyl-bicyclo[3.2.1]octan-3-one was described as having woody, fresh, minty, and menthol notes.

Example IV

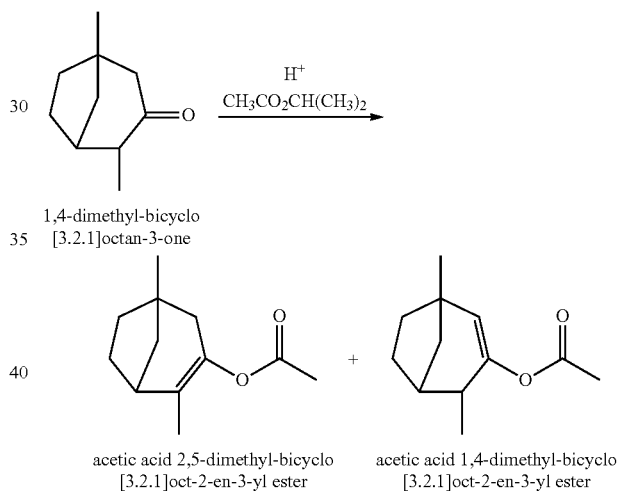

1,4-dimethyl-bicyclo [3.2.1]octan-3-one acetic acid 2,5-dimethyl-bicyclo [3.2.1]oct-2-en-3-yl ester     acetic acid 1,4-dimethyl-bicyclo [3.2.1]oct-2-en-3-yl ester Preparation of Acetic Acid 2,5-Dimethyl-bicyclo [3.2.1]oct-2-en-3-yl Ester (Structure II) and Acetic Acid 1,4-Dimethyl-bicyclo[3.2.1]oct-2-en-3-yl Ester (Structure III)

Para-toluenesulfonic acid (CH$_3$C$_6$H$_4$SO$_3$H, PTSA, 1 g) was added to a solution of 1,4-dimethyl-bicyclo[3.2.1]octan-3-one (100 g, 0.658 mol, obtained as above in EXAMPLE III) and isopropenyl acetate (CH$_3$CO$_2$CH(CH$_3$)$_2$, 300 g, 3 mol), and refluxed for 12 hours. The reaction mixture was subsequently washed with a Na$_2$CO$_3$ solution. Fractional distillation of the organic layer provided a mixture of acetic acid 2,5-dimethyl-bicyclo[3.2.1]oct-2-en-3-yl ester and acetic acid 1,4-dimethyl-bicyclo[3.2.1]oct-2-en-3-yl ester (127 g) having a boiling point of 60° C. at a pressure of 17 mmHg $^1$H NMR: 0.91 ppm (d, ~6% of 3H, J=7.2 Hz), 1.01 ppm (d, ~54% of 3H, J=6.9 Hz), 1.13 ppm (s, ~40% of 3H), 1.14 ppm (s, ~60% of 3H), 1.23 ppm (d, ~60% of 1H, J=10.8 Hz, of d, J=5.2 Hz), 1.34-2.33 ppm (m, 9H), 2.09-2.10 ppm (2s, 3H), 5.22 ppm (br, ~6% of 1H), 5.28 ppm (br, ~54% of 1H)

The mixture of acetic acid 2,5-dimethyl-bicyclo[3.2.1]oct-2-en-3-yl ester and acetic acid 1,4-dimethyl-bicyclo[3.2.1]oct-2-en-3-yl ester was described as having spicy, fruity, green, woody, and sweet notes with some fruitate characteristics.

Example V

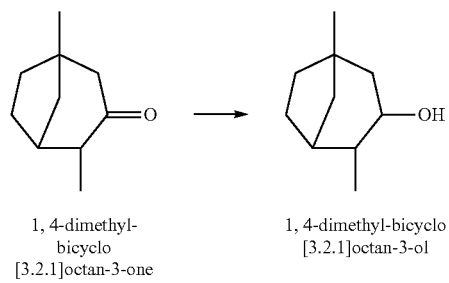

1, 4-dimethyl-bicyclo [3.2.1]octan-3-one 1, 4-dimethyl-bicyclo [3.2.1]octan-3-ol acetic acid 1, 4-dimethyl-bicyclo [3.2.1]oct-3-yl ester Preparation of Acetic Acid
1,4-Dimethyl-bicyclo[3.2.1]oct-3-yl Ester 1,4-Dimethyl-bicyclo[3.2.1]octan-3-one (260 g, 1.7 mol, obtained as above in EXAMPLE III) was added to a suspension of sodium borohydride (NaBH$_4$, 19 g, 0.5 mol) in isopropanol ((CH$_3$)$_2$CHOH, 400 mL), and refluxed for 30 minutes. The reaction mixture was cooled to room temperature, and quenched with acetone ((CH$_3$)$_2$CO) followed by acetic acid. The organic layer was separated and concentrated to provide crude 1,4-dimethyl-bicyclo[3.2.1]octan-3-ol (250 g, 1.6 mol), which was then added to a solution of acetic anhydride ((CH$_3$CO)$_2$O, 192 g, 1.9 mol) and Na$_2$CO$_3$ (4 g, 0.036 mol) and aged at 60° C. for 6 hours. The reaction mixture was subsequently washed with water followed by a Na$_2$CO$_3$ solution. Fractional distillation of the organic layer provided acetic acid 1,4-dimethyl-bicyclo[3.2.1]oct-3-yl ester (159 g) having a boiling point of 88° C. at a pressure of 15 mmHg $^1$H NMR: 0.83-0.94 ppm (m, 3H), 1.00-1.02 ppm (2s, 3H), 1.10-1.73 ppm (m, 7H), 1.76-1.86 ppm (m, 1H), 1.87-2.11 ppm (m, 2H), 2.01-2.03 ppm (2s, 3H), 4.52-5.18 ppm (m, 1H)

Acetic acid 1,4-dimethyl-bicyclo[3.2.1]oct-3-yl ester was described as having fruity, woody, and fresh notes.

Example VI

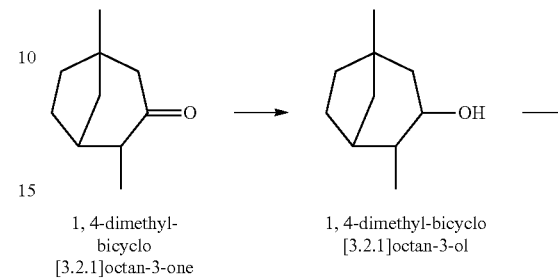

1, 4-dimethyl-bicyclo [3.2.1]octan-3-one 1, 4-dimethyl-bicyclo [3.2.1]octan-3-ol

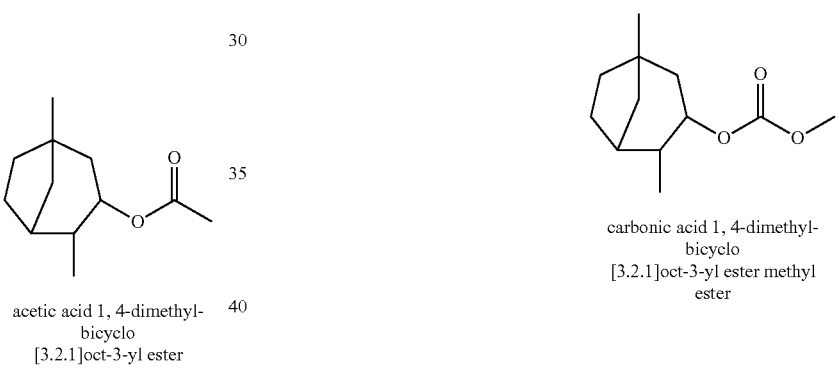

carbonic acid 1, 4-dimethyl-bicyclo [3.2.1]oct-3-yl ester methyl ester

Preparation of Carbonic Acid
1,4-Dimethyl-bicyclo[3.2.1]oct-3-yl Ester Methyl Ester (Structure V)

1,4-Dimethyl-bicyclo[3.2.1]octan-3-one (160 g, 1.05 mol, obtained as above in EXAMPLE III) was added to a NaBH$_4$ suspension (12 g, 0.33 mol) in isopropanol (200 mL), and refluxed for 30 minutes. The reaction mixture was cooled to room temperature, and quenched with acetone followed by acetic acid. The organic layer was separated and concentrated to provide crude 1,4-dimethyl-bicyclo[3.2.1]octan-3-ol (150 g, 1.0 mol), which was then added to dimethyl carbonate (CO(OCH$_3$)$_2$, 270 g, 3 mol), and potassium tert-butoxide ((CH$_3$)$_3$COK, 25 g), and refluxed for 3 hours. The volatile ingredients were removed with a Dean Stark trap. The reaction mixture was subsequently quenched with acetic acid, and washed with water. Fractional distillation of the organic layer provided carbonic acid 1,4-dimethyl-bicyclo[3.2.1]oct-3-yl ester methyl ester (125 g) having a boiling point of 65° C. at a pressure of 0.5 mmHg $^1$H NMR: 0.87-0.99 ppm (m, 3H), 1.00-1.10 ppm (2s, 3H), 1.22-2.18 ppm (m, 10H), 3.76 ppm (s, 3H), 4.36-5.20 ppm (m, 1H)

Carbonic acid 1,4-dimethyl-bicyclo[3.2.1]oct-3-yl ester methyl ester was described as having fruity and green notes.

Example VII

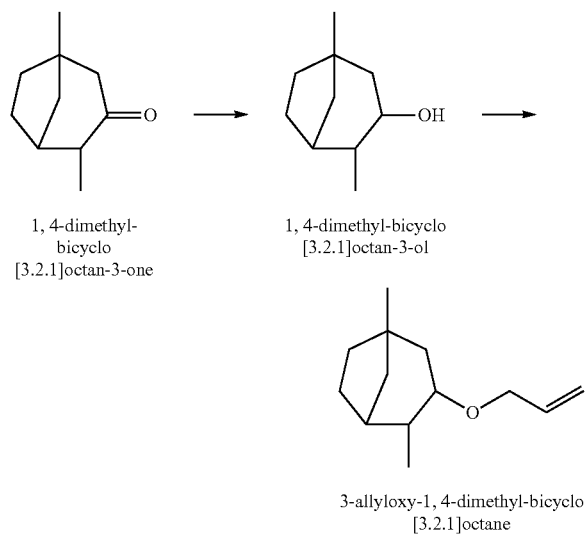

Preparation of
3-Allyloxy-1,4-Dimethyl-bicyclo[3.2.1]octane
(Structure VI)

1,4-Dimethyl-bicyclo[3.2.1]octan-3-one (325 g, 2.14 mol, obtained as above in EXAMPLE III) was added to a a $NaBH_4$ suspension (24 g, 0.64 mol) in isopropanol (600 mL), and refluxed for 30 minutes. The reaction mixture was cooled to room temperature, and quenched with acetone followed by acetic acid. The organic layer was separated and concentrated to provide crude 1,4-dimethyl-bicyclo[3.2.1]octan-3-ol (300 g, 1.9 mol), which was added to a solution of sodium amide ($NaNH_2$, 94 g, 2.4 mol) in tetrahydrofuran (THF, 1 L) while at reflux, and aged for 5 hours. Allyl chloride ($CH_2CHCH_2Cl$, 170 g, 2.2 mol) was subsequently added at 45° C. and aged for another 2 hours. The reaction mixture was subsequently washed with water and a $Na_2CO_3$ solution. Fractional distillation of the organic layer provided 3-allyloxy-1,4-dimethyl-bicyclo[3.2.1]octane (220 g) having a boiling point of 120° C. at a pressure of 30 mmHg $^1$H NMR: 0.87 ppm (d, ~25% of 3H, J=7.02 Hz), 0.96 ppm (d, ~75% of 3H, J=6.61 Hz), 1.04 ppm (s, 3H), 1.15 ppm (t, 1H, J=11.25 Hz), 1.20-1.60 ppm (m, 7H), 1.75-1.85 ppm (m, 1H), 1.90-1.95 ppm (m, 75% of 1H), 1.98-2.11 ppm (m, 25% of 1H), 3.00 ppm (m, ~75% of 1H), 3.57 ppm (m, ~25% of 1H), 3.89 ppm (m, 1H), 3.98 ppm (m, 25% of 1H), 4.07 ppm (m, 75% of 1H), 5.13 ppm (d, 1H, J=10.3 Hz), 5.25 ppm (d, 1H, J=16.5 Hz), 5.91 ppm (m, 1H)

3-Allyloxy-1,4-dimethyl-bicyclo[3.2.1]octane was described as having fruity, green, dirty, harsh, metallic, slight woody, camphor, juicy, acetophenone-like, and fenchol-like notes.

Example VIII

Establishment of Malodor Models

It is known that the perspirative malodors of human body, particularly sweat, are associated with the production of several unpleasant smelling organic acids, particularly isovaleric acid ("IVA"). The commercial sample of this malodorous material (commercially available at Sigma-Aldrich Inc.) was thus used as a model compound to assess the effectiveness of sweat malodor counteractants. The mold/mildew malodor model was prepared based on applicant's proprietary formulations for assessing the effectiveness of mold/mildew malodor counteractants.

Preparation of Test Samples

Two aluminum dishes were placed in an 8 oz glass jar. A malodor material was pipetted into one aluminum dish, and a compound of the present invention diluted in a solvent (10%) or a solvent alone control was pipetted into the other aluminum dish. The jar was then capped and the samples were allowed to equilibrate for one hour before the testing.

Testing Procedure

Test samples were presented in a blind and random order to 15-18 internal panelists (consisting of men/women with an age range of 25 to 55). However, different odor samples were arranged in an alternative order (for example, sweat, mold/mildew, sweat, mold/mildew, and etc.).

The panelists were instructed to take the steps of i) sniff jars containing only the malodor materials for familiarization prior to the testing; ii) uncap a jar; iii) place their noses at a distance of about 3-4 inches above the opening; iv) take short sniffs for 3 seconds; and v) provide a rank of the malodor coverage using an intensity scale of 1 to 5, where 1 represents "No Coverage", 3 represents "Moderate Coverage", and 5 represents "Excellent Coverage". The means for each sample was then calculated.

Results and Discussion

The mean ranks of the malodor coverage for the above test were as follows:

| | Compound (10%) | | | | Control |
|---|---|---|---|---|---|
| | Structure I | Structure II/III | Structure IV | Structure V | Solvent-Only |
| Vapor Pressure (µg/L) | 28652 | 490 | 1091 | 406 | |
| Sweat Malodor | 3.90 | 3.48 | 3.09 | 2.42 | 1 |
| Mold/Mildew Malodor | 3.32 | 3.37 | 2.96 | 2.49 | 1 |

Compounds of the present invention (Structures I-V) were demonstrated effective in counteracting sweat and mold/mildew malodors.

What is claimed is:

1. A method of counteracting a malodor in air space or a substrate comprising the step of introducing a malodor counteracting effective amount of a compound of formula:

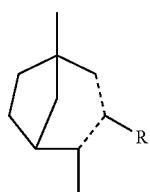

wherein R is acetate;

and wherein the broken line represents a single or double bond.

2. The method of claim 1, wherein the compound is selected from the group consisting of acetic acid 2,5-dimethyl-bicyclo[3.2.1]oct-2-en-3-yl ester;

acetic acid 1,4-dimethyl-bicyclo[3.2.1]oct-2-en-3-yl ester; and a mixture thereof.

3. The method of claim 2, wherein the compound is a mixture of acetic acid 2,5-dimethyl-bicyclo[3.2.1]oct-2-en-3-yl ester and acetic acid 1,4-dimethyl-bicyclo[3.2.1]oct-2-en-3-yl ester.

4. The method of claim 1, wherein the compound is used in a malodorous solid or liquid functional product, and wherein the malodor counteracting effective amount is from about 0.005% to about 50% by weight.

5. The method of claim 1, wherein the compound is used in a malodorous solid or liquid functional product, and wherein the malodor counteracting effective amount is from about 0.01% to about 20% by weight.

6. The method of claim 1, wherein the compound is used in a malodorous solid or liquid functional product, and wherein the malodor counteracting effective amount is from about 0.05% to about 5% by weight.

7. The method of claim 1, wherein the malodor is in air space, and wherein the malodor counteracting effective amount is from about 0.1 to 10 mg per cubic meter of air.

* * * * *